United States Patent [19]

Yalkowsky

[11] 4,301,175
[45] Nov. 17, 1981

[54] E-TYPE PROSTAGLANDIN COMPOSITIONS

[75] Inventor: Samuel H. Yalkowsky, Portage, Mich.

[73] Assignee: The Upjohn Company, Kalamazoo, Mich.

[21] Appl. No.: 220,599

[22] Filed: Dec. 29, 1980

[51] Int. Cl.³ .................. A61K 31/215; A61K 31/19
[52] U.S. Cl. ..................................... 424/305; 424/317
[58] Field of Search ............................. 424/317, 305

Primary Examiner—Sam Rosen
Attorney, Agent, or Firm—Lawrence T. Welch

[57] ABSTRACT

PGE-type compounds are stabilized in a composition comprising a mixture of triacetin and ethanol. This composition surprisingly and unexpectedly retains virtually all of the stability of triacetin compounds and additionally provides the superior water miscibility of ethanol.

16 Claims, No Drawings

E-TYPE PROSTAGLANDIN COMPOSITIONS

DESCRIPTION

BACKGROUND OF THE INVENTION

The present invention relates to novel compositions of matter. More particularly, the present invention relates to stable, water miscible pharmaceutical compositions. Most particularly, the present invention relates to stable, rapidly water miscible compositions of PGE-type compounds.

The prostaglandins are a family of 20 carbon atom fatty acids, being structural derivatives of prostanoic acid, which exhibit useful activity in a wide variety of biological systems. Accordingly, such prostaglandins represent useful pharmacological agents in the treatment and prevention of a wide variety of disease conditions. Prostanoic acid has the carbon atom numbering and structure as shown by formula I, below. A trivial system of nomenclature has been devised, which classifies the prostaglandins according to the substituents on the cyclopentane ring. See, N. A. Nelson, Journal of Medicinal Chemistry, 17:911 (1974). The terms "PGE-type compounds" or "E-type prostaglandins" are used to describe structural analogs of the prostaglandins having the substituents around the cyclopentane ring as shown in formula II, below. The formula II compound named is $PGE_2$. For a fuller discussion of the prostaglandins, see Bergstrom, et al., Pharmacol. Rev. 20:1 (1968) and references cited therein. For a further discussion of the uses of the E-type prostaglandins, see, e.g., U.S. Pat. No. 3,966,962, and references cited therein.

The problem in formulating prostaglandin compounds of the E series is the lack of stability of the compounds. These compounds tend to decompose, especially at room temperature (25° C.) and higher, and especially in the presence of small amounts of acid or base. Reasonable stability of prostaglandin compounds of the E series can be obtained by maintaining the temperature of the compound at −20° C. or lower. However, storage under such temperature conditions is usually inconvenient when the compounds are being used for the pharmacological purposes referred to above. Some limited success has been achieved by dissolving the prostaglandin in solvents such as ethyl acetate, chloroform, and ethanol. See, e.g., U.S. Pat. Nos. 3,749,800; 3,826,823; 3,829,579; and 3,851,052. However, these solutions do not provide long-term stability at room temperature. Solutions of PGE compounds in ethanol, for example, are not stable above 4° C.

Triacetin solutions are relatively stable at room temperature and higher. However, triacetin is very bitter tasting, making it unsuitable for oral administration alone. Much of the bitter taste of triacetin is removed by dissolving it in water. However, triacetin takes a relatively long time to dissolve in water (e.g., 60 seconds or more). Triacetin's poor water miscibility can thus result in incomplete doses of the drug being administered due to poor patient compliance (e.g., failure to dissolve the drug completely and the like).

Ethanol is instantly miscible with water, but, as noted above, solutions of PGE compounds in ethanol are unstable above 4° C.

Thus, each of the prior art solvents has certain drawbacks for oral administration.

PRIOR ART

A stable dosage form of a prostaglandin-like compound of the PGE-type comprising a solution of said compound in triacetin is disclosed in U.S. Pat. No. 3,966,962. A means of dispensing prostaglandin $E_2$ is disclosed in U.S. Pat. No. 3,749,800 which comprises dissolving the PGE compound in an anhydrous, water miscible, pharmacologically acceptable alcohol containing not more than 1.0% water.

SUMMARY OF THE INVENTION

The present invention particularly provides
(1) a stable, rapidly water miscible composition comprising
   (a) an amount of a stabilizing rapidly water miscible vehicle consisting essentially of ethanol and triacetin in a volume to volume ratio from about 1:3 to about 3:1; and
   (b) a quantity of an E-type prostaglandin which when dissolved in said amount of said vehicle is present therein in a concentration of less than about 100 mg/ml;
(2) a stable, rapidly water miscible pharmaceutical composition comprising
   (a) a unit dose of an E-type prostaglandin;
   (b) a quantity of a stabilizing rapidly water miscible vehicle consisting essentially of ethanol and triacetin in a volume to volume ratio from about 1:3 to about 3:1 such that said unit dose of said E-type prostaglandin is dissolved in said vehicle at a concentration less than about 100 mg/ml;
(3) in a stable pharmaceutical composition comprising an E-type prostaglandin and triacetin, the improvement which comprises ethanol in an amount of about one to about 3 parts by volume per part by volume of triacetin, whereby there is obtained a stable and rapidly water miscible E-type prostaglandin composition;
(4) in a rapidly water miscible pharmaceutical composition comprising an E-type prostaglandin and ethanol, the improvement which comprises:
triacetin in an amount of about one to about 3 parts by volume per part by volume of ethanol, whereby there is obtained a stable and rapidly water miscible E-type prostaglandin composition.

The present invention also provides a method for administering an E-type prostaglandin which comprises dissolving a composition or unit dose, as described above, in water.

Surprisingly and unexpectedly the composition of the present invention maintains virtually all of the stability possessed by the triacetin composition of the prior art, while it also has the rapid water miscibility attributed to the ethanol. This synergistic prostaglandin composition is thus much more suitable for liquid (e.g., oral and parenteral) administration than the prior art compositions.

By "E-type prostaglandins" is meant all prostaglandins of the E series which are useful for pharmacological purposes. These compounds are described for example in U.S. Pat. Nos. 3,639,463; 3,759,978; 3,767,695; 3,781,325; 3,804,889; 3,812,179; 3,818,433; 3,833,640; 3,835,180; 3,842,118; 3,847,966; 3,849,487; 3,855,270; 3,864,387; and 3,966,962. See also German Offenlegungsschriften Nos. 1,937,675; 1,937,921; 2,011,969; 2,036,471; 2,118,686; 2,121,980; 2,144,048; 2,150,361; 2,154,309; 2,165,184; 2,209,990; 2,217,044; 2,221,443;

2,317,019; 2,320,673; 2,332,400; 2,345,685; 2,432,155; and 2,423,156.

Preferred PGE-type compounds are:
PGE$_2$;
15R, 15-methyl-PGE$_2$;
16,16-dimethyl-PGE$_2$;
16,16-dimethyl-PGE$_2$, methyl ester;
16,16-dimethyl-trans-delta-2-PGE$_1$, methyl ester;
2-decarboxy-2-hydroxymethyl-PGE$_1$;
16,16-dimethyl-PGE$_2$, p-(p-acetamidobenzamido)-phenyl ester;
16,16-dimethyl-PGE$_2$, p-benzaldehyde semicarbazone ester; and
4,5,6-trinor-3,7-inter-m-phenylene-3-oxa-PGE$_1$.

By "stability" is meant the ability of the composition to substantially avoid decomposition at temperatures of from 25° to 35° C., for an extended period (e.g., six months).

By "rapidly water miscible" is meant the ability of the composition to dissolve in water at a pharmaceutically acceptable rate. Typically, dissolution times of 30 seconds or less are pharmaceutically acceptable.

By "Unit dose" is meant a discrete quantity of a stable, rapidly water miscible E-type prostaglandin composition useful for administering for various medical and veterinary purposes. Thus, an ideal unit dose would be one wherein one unit, or an integral amount thereof, contains the precise amount of prostaglandin for a particular purpose. These unit doses can be packaged in a variety of forms, e.g., hard gelatin capsules, foil packets, glass ampules, and the like. Similarly, a unit dose may be delivered from a medicine dropper or from a pump spray. These various unit doses may then be administered in various pharmaceutically acceptable forms of liquid administration, i.e., orally or parenterally. Thus, for example, the contents of a foil packet may be dissolved in water and ingested orally, or the contents of a glass vial may be injected. Similarly, a discrete amount from a medicine dropper or a pump spray may be dissolved in water.

While combinations of triacetin/ethanol of from 25%/75% to 75%/25%, respectively, may be employed in the present invention, it is preferred to employ a ratio of 50%/50% (1:1) to obtain the maximum amount of stability and water miscibility. Similarly, while the novel prostaglandin formulations of the present invention are administered to the animal or human subject by any of the routes known to be useful for the administration of PGE-type prostaglandins, the most preferred route of administration of the formulation of the present invention is orally. It is also advantageous to employ the compositions of the present invention for parenteral administration.

In utilizing the compositions of the present invention in pharmaceutical formulations, small amounts of flavoring agents, coloring agents or other pharmaceutical excipients may be added for pharmaceutical elegance.

While the triacetin/ethanol vehicle used for the composition of the present invention may be utilized for all concentrations of the PGE-type compound below 100 mg/ml, it is preferred to employ it below 1 mg per ml. This is preferred for ease of administration in light of the usual dosage of PGE-type compound employed.

The compositions of the present invention may be dissolved in water. While there should be sufficient water such that the composition is in solution, and not so much that it is inconvenient for oral administration, any quantity of water between these two limits may be employed in the method of this invention. It is preferred for ease of administration that a quantity of water from 10 to 1000 times the volume of the composition be employed, assuming the concentration of PGE type compound is less than 1 mg per ml.

A unit dose of the E-type prostaglandin ranges from 0.1 ξg to 2 mg per kg of body weight, and is administered from one to 5 times daily. The actual dosage regimen depends on a variety of factors including the purpose for which the E-type prostaglandin is employed, and the type, age, variety, sex, and medical condition of the mammal to which it is administered.

DESCRIPTION OF THE PREFERRED EMBODIMENTS

The operation of the present invention is seen more fully by the example given below:

EXAMPLE

Ten ml samples of triacetin, ethanol, and a one to one mixture of the two each containing approximately 5 mg per ml of PGE$_2$ (see Table I for exact values) were placed at 35° C. and at ambient temperature with protection from light for a six month period. The samples were evaluated on a periodic basis using HPLC (high performance liquid chromatography) analysis. The results are given in Tables I and II for ambient and 35° C. storage, respectively. Replicate analyses were performed for each time period, as expressed in the table. Table III shows the time required for dissolution of 0.1 ml of the solvent in 30 ml of water.

As can be seen from the Tables, surprisingly and unexpectedly the composition of the present invention retains virtually all of the desirable properties of both of the prior art compositions. Thus, the composition is both stable and rapidly water miscible.

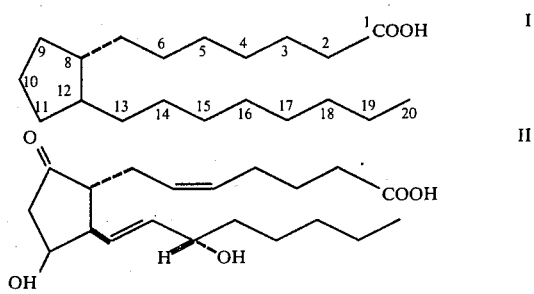

TABLE I

| % Triace-tin/Ethanol | Mg of PGE$_2$/ml | HPLC Assay Results - Ambient Storage Weeks | | | | | | | | | |
|---|---|---|---|---|---|---|---|---|---|---|---|
| | | 0 | 2 | 4.3 | 6 | 8 | 10 | 12 | 16 | 20 | 24 |
| 0/100 | 4.9996 | 5.02 | 4.95 | 4.97 | 4.88 | 4.67 | 4.50 | 4.31 | 4.05 | 4.02 | 3.83 |
| | | 5.10 | 4.97 | 4.97 | 4.86 | 4.67 | 4.42 | 4.37 | 4.03 | 4.09 | 3.76 |
| | | 5.11 | | | | | | | | | |
| | | 5.03 | | | | | | | | | |
| 50/50 | 5.0100 | 5.10 | 4.98 | 5.07 | 4.95 | 4.91 | 4.84 | 4.89 | 4.62 | 4.62 | 4.67 |

TABLE I-continued

| % Triacetin/Ethanol | Mg of PGE$_2$/ml | HPLC Assay Results - Ambient Storage |||||||||||
|---|---|---|---|---|---|---|---|---|---|---|---|
| | | Weeks ||||||||||
| | | 0 | 2 | 4.3 | 6 | 8 | 10 | 12 | 16 | 20 | 24 |
| | | 5.13 | 5.07 | 5.04 | 5.01 | 4.83 | 5.02 | 4.90 | 4.61 | 4.64 | 4.67 |
| | | 5.08 | | | | | | | | | |
| | | 5.01 | | | | | | | | | |
| 100/0 | 5.0192 | 4.89 | 4.97 | 4.93 | 4.90 | 4.94 | 4.83 | 4.84 | 4.70 | 4.84 | 4.90 |
| | | 4.95 | 4.95 | 4.96 | 4.88 | 4.90 | 4.88 | 4.86 | 4.73 | 4.79 | 4.77 |
| | | 4.92 | | | | | | | | | |
| | | 4.94 | | | | | | | | | |

TABLE II

| % Triacetin/Ethanol | Mg of PGE$_2$/ml | HPLC Assay Results - 35° C. Storage |||||||||||
|---|---|---|---|---|---|---|---|---|---|---|---|
| | | Weeks ||||||||||
| | | 0 | 2 | 4.3 | 6 | 8 | 10 | 12 | 16 | 20 | 24 |
| 0/100 | 4.9996 | 5.02 | 4.67 | 4.23 | 4.02 | 3.91 | 3.70 | 3.31 | 2.86 | 2.46 | 2.23 |
| | | 5.10 | 4.66 | 4.25 | 4.08 | 3.92 | 3.61 | 3.45 | 2.81 | 2.58 | 2.23 |
| | | 5.11 | | | | | | | | | |
| | | 5.03 | | | | | | | | | |
| 50/50 | 5.0100 | 5.10 | 4.85 | 4.77 | 4.52 | 4.52 | 4.56 | 4.39 | 4.02 | 3.87 | 3.55 |
| | | 5.13 | 5.04 | 4.69 | 4.56 | 4.50 | 4.50 | 4.36 | 4.04 | 3.96 | 3.51 |
| | | 5.08 | | | | | | | | | |
| | | 5.01 | | | | | | | | | |
| 100/0 | 5.0192 | 4.89 | 5.01 | 4.84 | 4.89 | 4.65 | 4.67 | 4.78 | 4.58 | 4.49 | 4.62 |
| | | 4.95 | 4.93 | 4.80 | 4.72 | 4.69 | 4.86 | 4.77 | 4.61 | 4.65 | 4.71 |
| | | 4.92 | | | | | | | | | |
| | | 4.94 | | | | | | | | | |

TABLE III

| Time required for dissolution of 0.1 ml of solvent in 30 mls of water (values are equal to or less than) | | |
|---|---|---|
| Triacetin/Ethanol (Solvent) | Rapid Stirring (Seconds) | Gentile Swirling (Seconds) |
| 100/0 | 60 | 120 |
| 50/50 | 3 | 10 |
| 0/100 | Instantly | Instantly |

I claim:

1. A stable, rapidly water miscible composition comprising
   (a) an amount of a stabilizing rapidly water miscible vehicle consisting essentially of ethanol and triacetin in a volume to volume ratio from about 1:3 to about 3:1; and
   (b) a quantity of an E-type prostaglandin which when dissolved in said amount of said vehicle is present therein in a concentration of greater than zero and less than about 100 mg/ml.

2. A stable, rapidly water miscible pharmaceutical composition comprising
   (a) a dose of an E-type prostaglandin;
   (b) a quantity of a stabilizing rapidly water miscible vehicle consisting essentially of ethanol and triacetin in a volume to volume ratio from about 1:3 to about 3:1 such that said dose of said E-type prostaglandin is dissolved in said vehicle at a concentration greater than zero and less than about 100 mg/ml.

3. In a stable pharmaceutical composition comprising an E-type prostaglandin and triacetin, the improvement which comprises ethanol in an amount of about one to about 3 parts by volume per part by volume of triacetin, whereby there is obtained a stable and rapidly water miscible E-type prostaglandin composition.

4. In a rapidly water miscible pharmaceutical composition comprising an E-type prostaglandin and ethanol, the improvement which comprises:
   triacetin in an amount of about one to about 3 parts by volume per part by volume of ethanol, whereby there is obtained a stable and rapidly water miscible E-type prostaglandin composition.

5. A composition of claim 1 or claim 2 wherein the concentration of the E-type prostaglandin is less than 1 mg/ml.

6. A composition of claim 5, wherein the concentration of ethanol is 50% and the concentration of triacetin is 50%.

7. A composition of claim 6, wherein the PGE-type compound is PGE.

8. A composition of claim 6, wherein the PGE-type compound is 15R,15-methyl-PGE$_2$.

9. A composition of claim 6, wherein the PGE-type compound is 16,16-dimethyl-PGE$_2$.

10. A composition of claim 6, wherein the PGE-type compound is 16,16-dimethyl-PGE$_2$, methyl ester.

11. A composition of claim 6, wherein the PGE-type compound is 16,16-dimethyl-trans-delta-2-PGE$_1$, methyl ester.

12. A composition of claim 6, wherein the PGE-type compound is 2-decarboxy-2-hydroxymethyl-PGE$_1$.

13. A composition of claim 6, wherein the PGE-type compound is 16,16-dimethyl-PGE$_2$, p-(p-acetamidobenzamido)phenyl ester.

14. A composition of claim 6, wherein the PGE-type compound is 16,16-dimethyl-PGE$_2$, p-benzaldehyde semicarbazone ester.

15. A composition of claim 6, wherein the PGE-type compound is 4,5,6-trinor-3,7-inter-m-phenylene-3-oxa-PGE$_1$.

16. A method for orally administering an E-type prostaglandin which comprises dissolving a composition of claim 1 or claim 2 in water prior to administration.

* * * * *